United States Patent [19]

Nardella

[11] Patent Number: 4,462,799
[45] Date of Patent: Jul. 31, 1984

[54] DOUBLE SCREW FOR A FOUR PART ACTIVATOR IN JAW ORTHOPEDICS

[76] Inventor: Alessandro Nardella, Eggensteiner Str. 20, Stutensee, Fed. Rep. of Germany, D-7513

[21] Appl. No.: 487,137

[22] Filed: Apr. 21, 1983

[30] Foreign Application Priority Data

Apr. 21, 1982 [DE] Fed. Rep. of Germany ....... 3214844

[51] Int. Cl.$^3$ .............................................. A61C 3/00
[52] U.S. Cl. .......................................... 433/7; 433/19
[58] Field of Search .......................... 433/7, 18, 19, 24

[56] References Cited

U.S. PATENT DOCUMENTS

| 473,040 | 4/1892 | Wilder | 433/18 |
| 3,454,001 | 7/1969 | Stockfisch | 433/7 |
| 4,348,179 | 9/1982 | Nardella | 433/7 |

FOREIGN PATENT DOCUMENTS

| 1041207 | 10/1958 | Fed. Rep. of Germany | 433/7 |
| 1020995 | 2/1953 | France | 433/7 |

OTHER PUBLICATIONS

"Praktische Kieferorthopädie", Ascher, Urban & Schwarzenberg, 1968, pp. 110-111.

Primary Examiner—John J. Wilson
Attorney, Agent, or Firm—Burgess, Ryan & Wayne

[57] ABSTRACT

In a double screw where the four screws bearing activator parts are connected by a web, versatility of employment and tongue clearance are improved in that the web is of bipartite construction and its parts are interconnected by a joint whose axis of swing is parallel to the axes of the screws, the adjusted swing position of the web parts being fixable.

5 Claims, 6 Drawing Figures

DOUBLE SCREW FOR A FOUR PART ACTIVATOR IN JAW ORTHOPEDICS

BACKGROUND OF THE INVENTION

The invention relates to a double screw for a four-part activator intended for simultaneous independent activation of the upper and lower jaw, having a first expansion screw to be associated with the frontal and lateral dentition of the upper jaw and a second expansion screw parallel thereto, to be associated with the incisor and lateral dentition of the lower jaw, as well as a web connecting the two screws vertically to their axes.

Such a double screw is described in Professor Dr. Felix Ascher's book *Praktische Kieferothopadie*, Urban & Schwarzenberg, Munich-Berlin-Vienna 1968, p. 110 and 111. The screw is used when the differential compression in the upper and lower jaw is so high that the necessary expansion in the upper and lower lateral dentition can hardly be achieved by ordinary means. The double screw comprises two screws connected by a sturdy vertical web. One screw is located in the frontal division of the upper jaw, the other in the incisor division of the lower jaw. The connecting web is oriented with the center of the bite. The assembly is imbedded in the wax form of the activator. The single screws used are those employed in active expansion plates. The plate is parted at the midline and parallel to the occlusal plane, the biting groove for the lower incisors being retained in the lower jaw part of the plate structure. Four parts result, held together by the aforesaid vertical web.

The known double screw has the disadvantage that firstly the activator parts, for secure imbedding of the double screw, must be of massive construction, restricting the clearance for the tongue, and that secondly, owing to the preassigned size of the vertical web, in smaller jaws the double screw must be arranged farther away from the front teeth, further confining the lingual bed.

SUMMARY OF THE INVENTION

The object of the invention is so to improve the double screw of the kind initially mentioned that, using activator parts requiring less material, a universal employment of the double screw independently of jaw size can be attained as close as possible to the front teeth, in order to minimize interference with the tongue clearance.

In a double screw of the kind initially mentioned, this object is accomplished in that the web is bipartite and its parts are connected by an articulation whose axis of swing is parallel to the axes of the screws, the adjusted swing position of the web parts being fixable.

The double screw according to the invention has the advantage of permitting extremely versatile use and moreover leaving a surprisingly wide tongue clearance.

A smooth bipartite web with joint is obtained by a construction in which the web part of one screw has a projection with bore and the web part of the other screw has two lugs, each likewise bored, arranged laterally adjacent to the projection, a headed screw being passed through the holes, and at least the bore of the lug opposed to the head of the screw having an internal thread matching the screw thread.

The web parts are advantageously adjustable at an angle of from 70° to 270° to each other. With this angular range, a favorable adaptation to a given anatomical situation of the concavity of the anterior division of the oral cavity can be achieved.

Universal use of the double screw according to the invention is further facilitated because at least one of the expansion screws may be a transversely equi-acting adjustable screw. Further, at least one of the expansion screws may be a reciprocally adjustable pair of sectorial screws. In other words, the double screw may comprise transversly equi-acting expansion screws or reciprocally adjustable pairs of sectorial screws or a combination of such expansion screws.

DETAILED DESCRIPTION

The double screw according to the invention, by virtue of the vertical adjustable and fixable angular setting, permits the provision of a gracile lingual bed. In the transversal, it is possible to perform alterations of tooth position in each quadrant singly, and this with a finely proportionable force, and anchorage of two-thirds of the double screw. The double screw according to the invention thus provides the possibility of individual adaptation to the given situation in a particular case.

The invention will be further illustrated with reference to the drawing by way of example. In the drawing, FIG. 1 shows a top view of one embodiment of a double screw;

FIG. 2 shows a top view of a second embodiment of a double screw;

FIG. 3, in a side view of a double screw, illustrates the range of swing of the web parts relative to each other;

Figure 1:
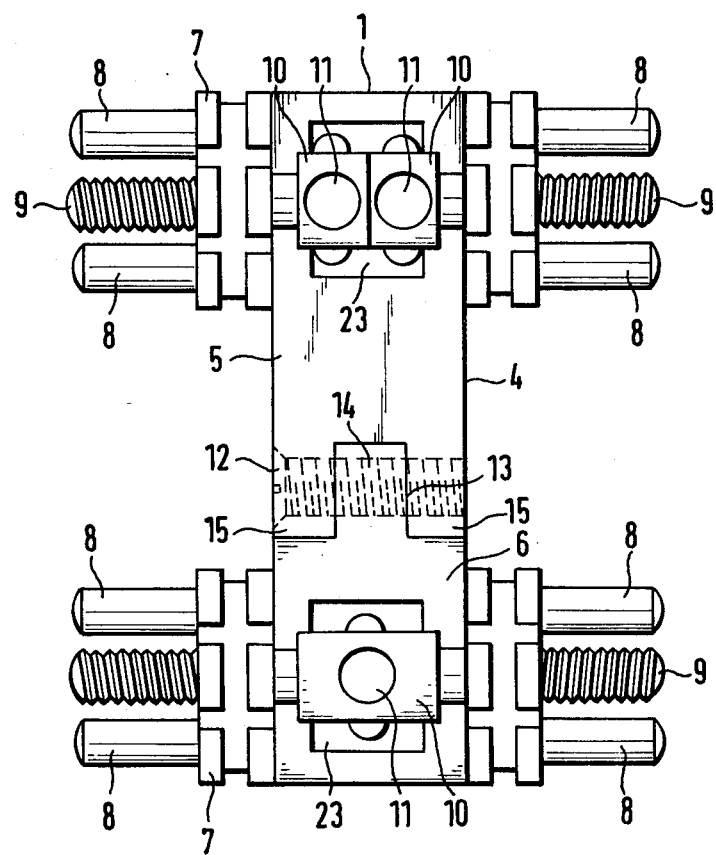

The double screw 1 shown in FIG. 1 has a web 4 consisting of a part 5 and a part 6.

The web part 5 has a retention member 7. The retention member 7 has, on either side, two spaced holding pins 8 substantially perpendicular to the lengthwise extent of the web part 5. The web part 6 is similarly provided with a retention member 7 and holding pins 8.

Each of the retention members, between the holding pins 8, has a threaded hole to receive an expansion screw 9, the head 10 of which with adjusting hole 11 is arranged in a recess 23 of the web part 5 or 6. The threads of the expansion screws 9 are opposite hand on either side of the head 10.

In the embodiment shown in FIG. 1 by way of example, the second web part 6 is associated with a transverse screw with single head 10, while the web part 5 is associated, by way of expansion screw, with a pair of sectorial screws having two heads 10, each with adjusting hole 11. The pair of sectorial screws of part 5 permits a reciprocal adjustment, and the expansion screw 9 of part 6 a transverse adjustment.

The web part 5, in its prolongation at the end opposed to that accommodating the retention member 7, has two lugs 15, traversed by a coaxial bore provided with an internal thread. The web part 6, in its prolongation at the end opposed to that accommodating the retention member 7, has a projection 14 with bore. When the projection 14 is arranged between the lugs 15, the bores are aligned, so that a countersunk screw 12 can be inserted, forming the joint 13. A setting of the joint is fixed by tightening the screw 12.

Figure 2:
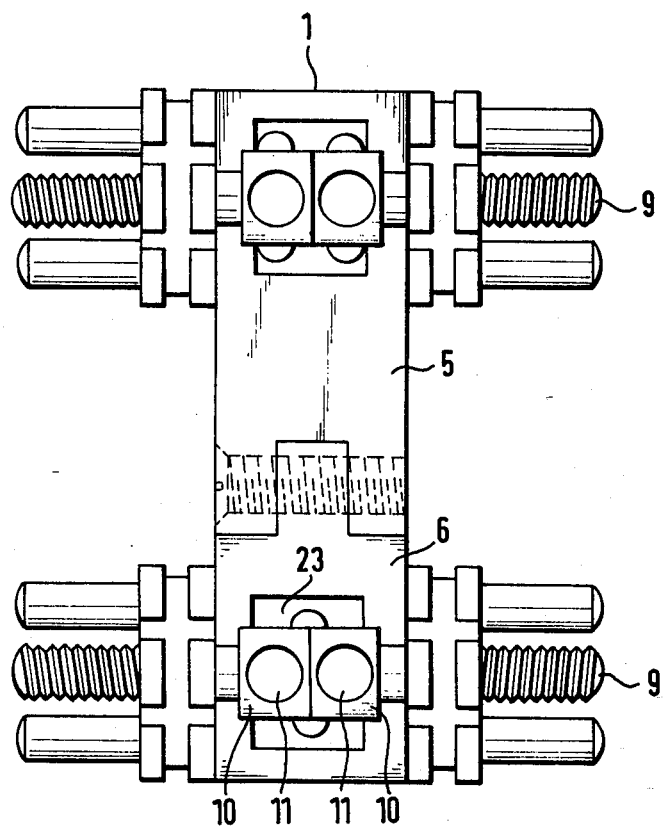

The embodiment of the double screw as shown in FIG. 2 is similar to the embodiment of FIG. 1 with the exception that the transverse expansion screw 9 associated with the web part 6 in FIG. 1 has been replaced by an additional reciprocal expansion screw, in other words by a pair of sectorial screws, as in the case of the web part 5 in FIG. 1, in each instance with two screw heads 10 each having an adjusting hole 11.

Figure 3:
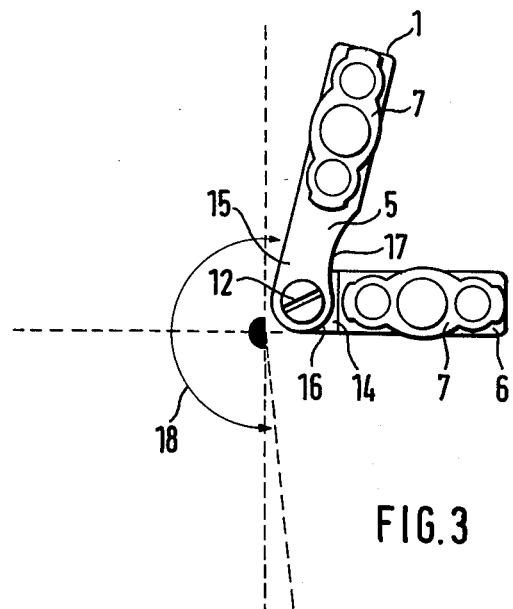

FIG. 3 shows the double screw 1 in one terminal position, in which the web parts 5 and 6 form an angle of 70° between them. Starting from this one setting, in which the web part 6 is to be fixed, the web part 5 can be swung 200° in the direction of the arc 18 in FIG. 3. This range of swing is made possible by the roundings 16 and 17 on web part 5. Thus the range within which the web parts 5 and 6 can be swung relative to each other extends from 70° to 270°.

Figures 4, 6:
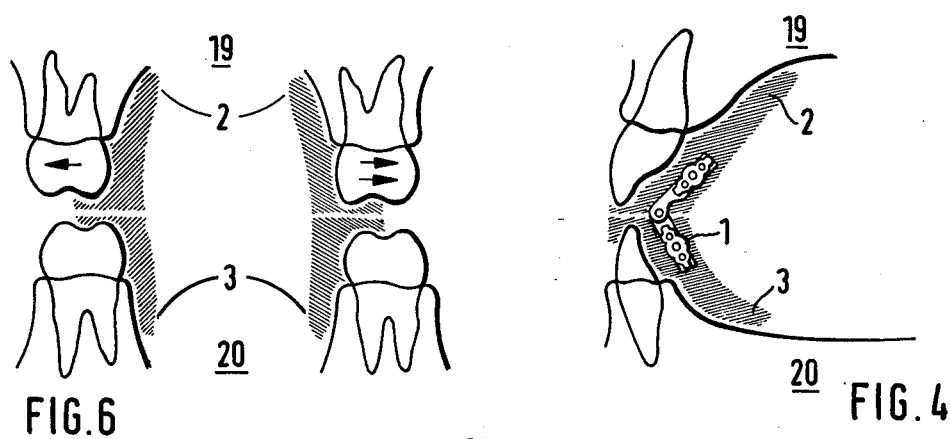
FIG. 4 shows the arrangement of the double screw imbedded in the activator parts, in median sagittal section.
FIG. 6 shows the activator parts fitted with the double screw, in dorsal view.
Figure 5:
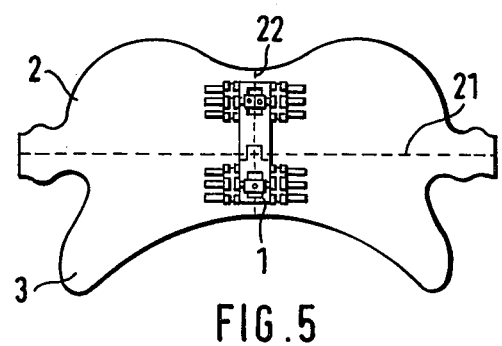
FIG. 5 shows the double screw with imbedding activator parts.

The double screw 1, as is shown for example in FIG. 5, is imbedded in activator parts 2 and 3, separated from each other by a horizontal parting line 21. Each of the activator parts 2 and 3 is subdivided along a vertical parting line 22, so that a four-part activator results. The parting line 22 lies in the parting plane of the double screw 1 with respect to transversal and reciprocal adjustment. The arrangement of the double screw 1 with activator parts 2 and 3 in the mouth between the upper jaw 19 and the lower jaw 20 is shown in FIGS. 4 and 6. In FIG. 4, it is seen that the available tongue clearance is surprisingly great. In the arrangement of the activator as seen in FIG. 6, a transversal or reciprocal adjustment of the respective suitably constructed expansion screw 9 can be effected in the region of the upper jaw 19, and the same applies to the activator part associated with the lower jaw 20.

I claim:

1. An orthopedic appliance adapted to be disposed in the mouth of a person for simultaneously acting upon the upper and lower jaw, said appliance comprising:
    a first web part having a screw-receiving end and a junction end longitudinally spaced from said screw-receiving end,
        said first web part having a first transverse hole therethrough at said screw-receiving end thereof;
    first expansion screw means for displacing the dentition of the upper jaw, said first expansion screw means extending through said first hole transversely of said first web part;
    first screw-turning means for rotating said first expansion screw means;
    a first pair of left and right retention members disposed transversely of said screw-receiving end of said first web part on opposite sides thereof, each of said first pair of left and right retention members having a threaded hole surrounding and threadably engaged with said first expansion screw means, so that the transverse spacing between each of said retention members and said first web part can be varied by rotation of said first expansion screw means;
    a second web part having a screw-receiving end and a junction end longitudinally spaced from said screw-receiving end,
        said second web part having a second transverse hole therethrough at said screw-receiving end thereof, said second transverse hole being substantially parallel to said first transverse hole;
    second expansion screw means for displacing the dentition of the lower jaw, said second expansion screw means extending through said second hole transversely of said second web part
    second screw-turning means for rotating said second expansion screw means;
    a second pair of left and right retention members disposed transversely of said screw-receiving end of said second web part on opposite sides thereof, each of said second pair of left and right retention members having a threaded hole surrounding and threadably engaged with said second expansion screw means, so that the transverse spacing between each of said retention members and said second web part can be varied by rotation of said second expansion screw means;
    hinge means pivotably interconnecting the junction ends of said first and second web parts for relative rotation about a transverse axis substantially parallel to said transverse holes in said web parts; and
    releasable hinge locking means operatively associated with said hinge means for preventing relative rotation of said web parts about said axis, thereby maintaining said web parts in a selected relative angular orientation.

2. The appliance according to claim 1, wherein at least one of said expansion screw means comprises two colinearly aligned screws each having its own screw-turning means.

3. The appliance according to claim 1, wherein the portions of at least one of said expansion screw means extending on opposite sides of the corresponding web part, bear threads of opposite hand.

4. The appliance according to claim 1, wherein said hinge means comprises a forked end on one of said web parts, a projection on the other of said web parts disposed between the tines of said forked end, a transverse pivot hole extending through said projection and tines, and a pivot pin element disposed in said pivot hole.

5. The appliance according to claim 4, wherein at least a portion of said pivot hole is internally threaded, and said pivot pin element comprises a screw also serving as said releasable hinge locking means.

* * * * *